United States Patent [19]

Heller et al.

[11] Patent Number: 4,685,783
[45] Date of Patent: * Aug. 11, 1987

[54] POLYCHROMIC TETRACYCLO-SPIRO-ADAMATYLIDENE DERIVATIVES, AND POLYCHROMIC LENS INCORPORATING SAID COMPOUNDS

[75] Inventors: Harold H. Heller, Cardiff; Stephen N. Oliver; John Whittal, both of Mid-Glamorgan, all of United Kingdom; William Johncock, Geneva, Switzerland; Paul J. Darcy, Aberystwyth; Clive Trundle, Towcester, both of United Kingdom

[73] Assignee: The Plessey Company P.L.C., Essex, England

[ * ] Notice: The portion of the term of this patent subsequent to Mar. 18, 2003 has been disclaimed.

[21] Appl. No.: 647,565

[22] Filed: Sep. 5, 1984

Related U.S. Application Data

[63] Continuation-in-part of Ser. No. 530,161, Sep. 7, 1983, abandoned.

[51] Int. Cl.$^4$ .................. C07D 307/60; C07D 405/06; C09K 9/00; G03C 1/733
[52] U.S. Cl. ..................... 351/163; 351/44; 351/166; 350/586; 549/41; 549/42; 549/44; 549/60; 548/407; 252/586
[58] Field of Search .................. 549/41, 42, 44, 60; 548/407; 252/586; 350/354; 351/44, 163, 166

[56] References Cited

U.S. PATENT DOCUMENTS 4,215,010  7/1980  Hovey et al. .................... 350/354
4,220,708  9/1980  Heller .......................... 549/60

FOREIGN PATENT DOCUMENTS 2002752  2/1979  United Kingdom ............... 549/60
2051813  1/1981  United Kingdom ............... 549/60

*Primary Examiner*—Henry R. Jiles
*Assistant Examiner*—J. G. Mullins

*Attorney, Agent, or Firm*—Sughrue, Mion, Zinn, Macpeak and Seas

[57] ABSTRACT

A series of photochromic compounds are disclosed which have the property of undergoing a reversible color change when exposed to unfiltered sunlight and reverting to their original color in the absence of U.V. light at room temperature. These compounds have the general formula:

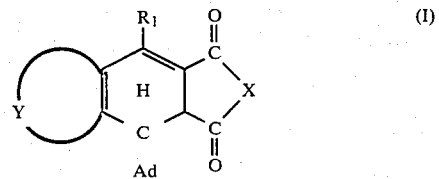

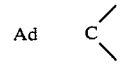

represents an adamantylidene or a substituted adamantylidene group;

$R_1$ represents hydrogen, alkyl, aryl, aralkyl or a heterocyclic group,

X represents oxygen or > $NR_2$, in which $R_2$ is hydrogen, aryl, alkyl or aralkyl and

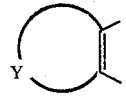

represents an aromatic group, an unsaturated heterocyclic group or a benzannelated heterocyclic group.

The photochromic compounds of the invention are useful in the manufacture of photoreactive lenses, particularly plastic lenses.

7 Claims, 13 Drawing Figures

EXAMPLES
1 R = Ph
2 R = H
3 R = Br
4 R = NO₂

SCHEME 1

SCHEME 3

EXAMPLE 7

SCHEME 4

EXAMPLE 8

SCHEME 5

EXAMPLE 9  R = Me
10  R = Ph
11  R = p-MeO.$C_6H_4$

SCHEME 6

EXAMPLES  12  R = Me
          13  R = Ph

SCHEME 7

EXAMPLE 14

SCHEME 8

EXAMPLE 15

SCHEME 10

EXAMPLE 17

POLYCHROMIC TETRACYCLO-SPIRO-ADAMATYLIDENE DERIVATIVES, AND POLYCHROMIC LENS INCORPORATING SAID COMPOUNDS

This is a continuation-in-part of application Ser. No. 530,161, filed Sept. 7, 1983, now abandoned.

BACKGROUND OF THE INVENTION

This invention relates to photochromic compounds and is particularly concerned with compounds having the ability to undergo a change to a coloured or more strongly coloured form in strong sunlight and revert to their original form on removal or reduction of the U.V. component of sunlight, e.g. in diffuse daylight conditions.

DESCRIPTION OF THE PRIOR ART

In general, known photochromic compounds absorb U.V. light to generate coloured forms but these tend to revert to the colourless form when exposed to white light and also undergo thermal fade at ambient temperatures. U.K. Patent Specification No. 2,002,752 discloses a series of photochromic compounds having a high degree of photosensitivity so that they colour in U.V. light and reverse rapidly in white light. Such compounds are not suitable sunglasses or related applications because of this tendency to revert to the colourless form in white light. As a consequence, they show little or no colouring in unfiltered sunlight.

While it is possible to select compounds which have a low quantum efficiency for bleaching in white light this characteristic is usually associated with a coloured form which is thermally relatively stable so that reversion to the colourless form at normal ambient temperatures is very slow. As a result, such compounds would not be suitable in photo-reactive lenses.

A new class of photochromic compounds has been discovered which possess the combination of properties necessary for photoreactive lenses, namely (a) a high quantum efficiency for colouring in the near ultra-violet (b) a low quantum yield for bleaching with visible white light and (c) fast thermal fade at ambient temperatures, but not so rapid that the combination of white light bleaching and thermal fade prevent colouring by the ultraviolet component of strong sunlight. In addition, these properties are desirably retained in the conventional rigid plastics used for opthalmic and plano lenses.

The term "heliochromic" is introduced to describe the behaviour of these novel compounds and will be used for this purpose in the remainder of this specification.

SUMMARY OF THE INVENTION

According to one aspect of the present invention, there is provided a series of photochromic compounds of the general formula:

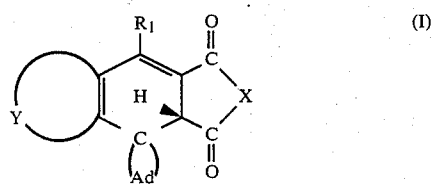 (I)

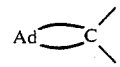

represents an adamantylidene or a substituted adamantylidene group;

$R_1$ represents hydrogen, alkyl, aryl, aralkyl or a heterocyclic group;

X represents oxygen or $>NR_2$, in which $R_2$ is hydrogen, aryl, alkyl, or aralkyl and

 (II)

represents an aromatic group, an unsaturated heterocyclic group or a benzannelated heterocyclic group. Examples of possible substituents in the adamantylidene group are halogen and hydroxy.

Preferred classes of heliochromic compounds falling within formula (I) are those in which the group represented by the formula (II):

 (II)

is a resonance stabilised heterocyclic group, containing an oxygen or sulphur heteroatom e.g. furyl or thienyl. Such heterocyclic groups may be benzannelated and substituted in positions other than where the group is linked to the six-membered group in formula (I), especially the α-position. Suitable substituents are deuterium, lower alkyl, e.g. methyl, ethyl, propyl, aryl (e.g. phenyl), nitro, and halogen, (e.g. chloro or bromo) groups.

Examples of aromatic or heterocyclic groups represented by the above formula (II) are groups derived from 2,5-, 2,4- or 3,5-dimethoxyphenyl; 2- or 3-furyl; or 2- or 3-thienyl groups, which may be substituted or benzannelated by cyclisation onto that group with a subsequent hydrogen shift.

The introduction of electron-withdrawing groups such as bromine in the furyl or thienyl group will cause a hypsochromic colour shift in the corresponding heliochromic compound. Also, the introduction of substituents (including benzannelation) in the furyl and thienyl ring tends to increase the resistance of the compounds to oxidation and thereby reduces the fatigue rate. Because fatigue reactions appear to proceed by an oxidative mechanism, it is also desirable to protect the compounds from oxygen in their ultimate application, e.g. by encapsulation or by use of oxygen scavengers, when employed in photoreactive lens manufacture.

The group represented by $R_1$ in the above formula (I) is preferably other than hydrogen e.g. substituted with a lower alkyl, i.e. methyl, ethyl, propyl or butyl (especially methyl) or phenyl. Preferred groups represented by $R_2$ are methyl and phenyl.

DETAILED DESCRIPTION-OF-THE-INVENTION

In the following description, reference will be made to the accompanying sheets of formulae drawings.

Heliochromic behaviour and compounds having structures falling within the general formula (I) above were discovered as a consequence of investigation of the effect of heating of fulgides. As noted in British Patent Specification No. 2,002,752, certain fulgides can be converted into their coloured forms by heating. The reaction was found to be reversible using white light and the coloured form was found to be stable in the dark at room temperature. No value was perceived in these fulgides for sunglass applications because their photochromic response to sunlight was generally poor.

Figure 1:
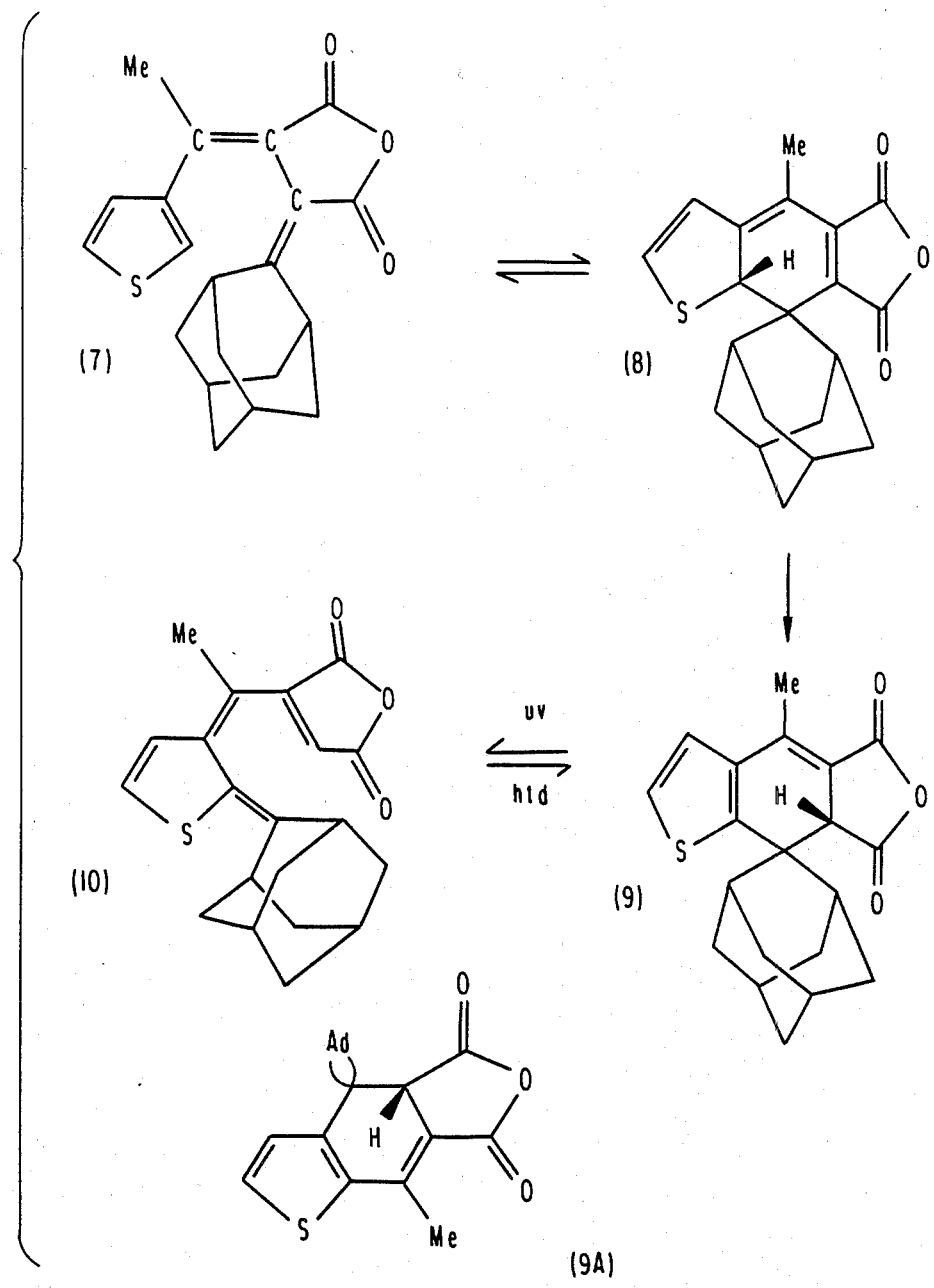

Nevertheless, these remarkable photochromic properties prompted further investigation of the reactions because of the present inventors' interest in the fundamental chemistry of fulgides and their corresponding coloured forms. As a consequence of these investigations, it was found that certain fulgides containing an adamantylidene group underwent a photochemical or thermal ring closure and a thermal 1,5-hydrogen shift to give compounds which surprisingly exhibited heliochromic properties. For example, in the case of adamantylidene [α-3-thienyl)ethylidene] succinic anhydride (structure 7 in FIG. 1 of the accompanying drawings) heating at about 140° C., caused ring closure to the coloured cyclic form (structure 8) which underwent a 1,5-hydrogen shift to the cyclic structure (9) (particularly at temperatures of about 180° C.). While fulgide (7) is not heliochromic, the colourless cyclic structure (9) is heliochromic. On irradiation with ultraviolet light in solution in toluene (even in the presence of white light), it gives the purple/blue coloured form (structure 10) which reverses to the colourless form (structure 9) at ambient temperatures in the absence of u.v. stimulation. Because the coloured form (10) exhibits such a very slow white light reversal, coupled with a relatively fast thermal fade at ambient temperatures, it is potentially valuable for use in photoreactive lenses.

The adamantylidene group possesses a rigid strain free cage structure. Its structure is shown in the accompanying formula drawings. For convenience, the informal shorthand form,

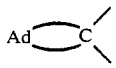

is used in this specification to designate the adamantylidene group as indicated at the foot of sheets 3 to 10 of the formula drawings. It is believed that the adamantylidene group plays a vital part in the generation of the heliochromic properties of this invention, because this bulky, stable group weakens the single bond of the six-membered ring of which it forms part, facilitating electrocyclic ring opening on irradiation with ultra-violet light. Attempts have been made to substitute other bulky groups for the adamantylidene group but there appear to be few practical alternative groups. For example, camphor and fenchone would appear at first sight to be suitable alternatives but these ketones failed to undergo the Stobbe reaction, probably because of steric hindrance. Simpler acyclic cyclic and bicyclic ketones do undergo the Stobbe reaction and the corresponding half esters can be hydrolysed to the diacids and hence to the corresponding fulgides. Although the latter are often photochromic, heating does not produce a heliochromic derivative.

The adamantylidene group need not be attached to the group

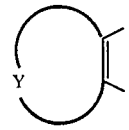

where this represents a heterocyclic group, via the carbon atom adjacent to the heteroatom. For example, referring to structural formula 9 (sheet 1 of the drawings) the adamantylidene group need not be attached to the thienyl group via the 2-position but could equally be attached via the 3-position as shown in structural formula (9A).

Figure 2:
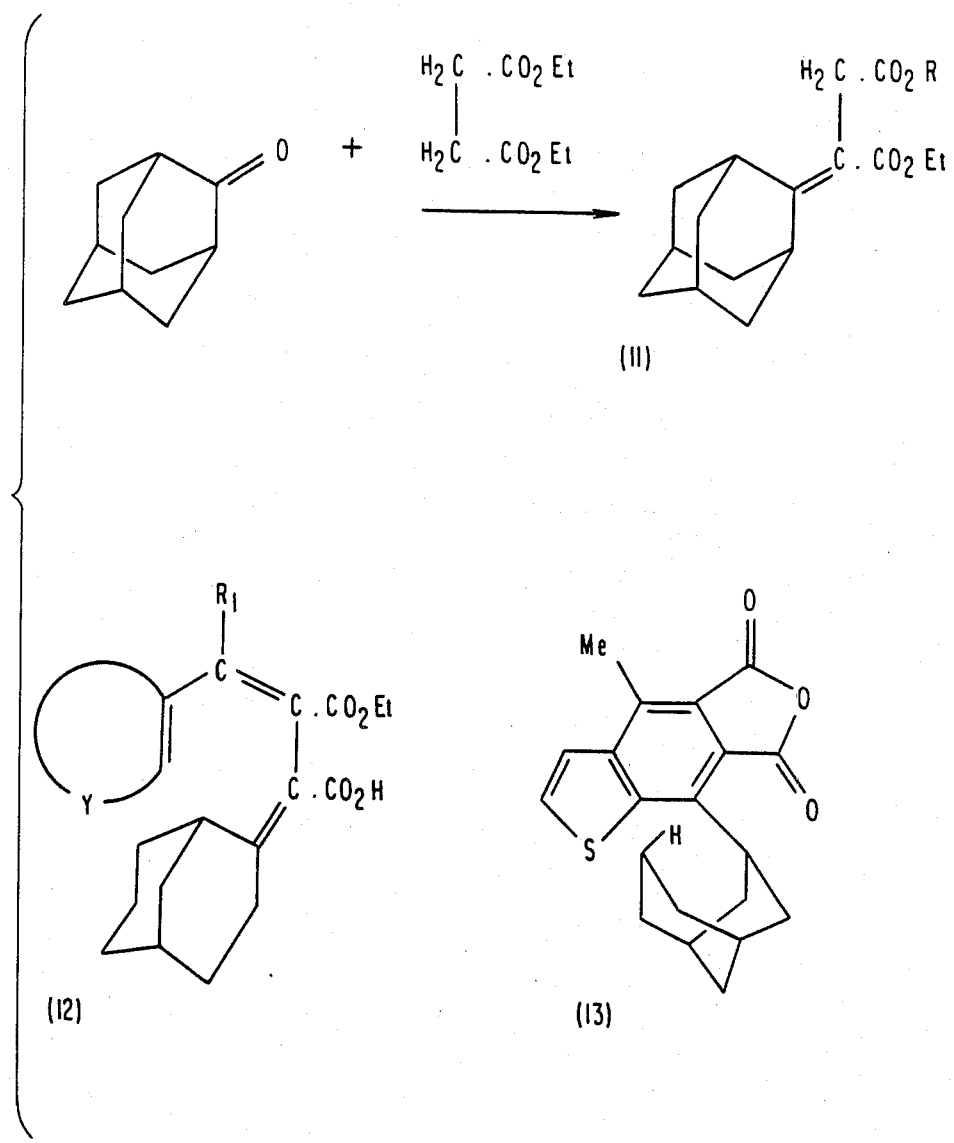

The preparation of the fulgides from which the heliochromes are obtained is conveniently carried out using a dialkyl adamantylidenesuccinate (preferably the diethyl ester) as the starting material. The preparation of this ester is described in U.K. Patent Specification No. 2,051,813 and can be obtained in over 80% yield and more than 98% purity. The reaction scheme on FIG. 2 in the accompanying drawings indicates the reaction and the structure of the diester (structure 11, where R=Et). Preferrred reaction conditions involve condensation of adamantanone with diethyl succinate in the presence of a condensing agent, such as sodium hydride (as 50% dispersion in oil) or potassium t-butoxide (in t-butanol), followed by esterification of the half ester (structure 11), where R=H) using an ethanol/toluene mixture and toluene-p-sulphonic acid as catalyst. The adamantylidene diester is condensed with the appropriate aldehyde or ketone

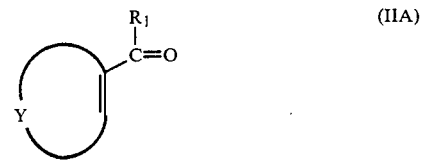

wherein $R_1$ has the same significance as in formula (I) above) in the presence of a condensing agent, as before, followed by hydrolysis of the resulting half ester (structure 12) to the diacids, e.g. with 10% ethanolic potassium hydroxide solution.

The E-diacid is obtained in admixture with the Z-isomer, by hydrolysis, e.g. with 10% ethanolic potassium hydroxide solution. The diacids are cyclised with an appropriate agent, e.g. acetic anhydride or acetyl chloride to form the corresponding fulgides. The heliochromic rearrangement product is obtained by heating the fulgides or fulgimides or by a combination of heating and irradiation with U.V. light or by Lewis acid-catalysed cyclisation, e.g. using $SnCl_4$. A combination of U.V. irradiation and heating has the advantage that a lower temperature can be employed and under such milder conditions a better yield can be anticipated. Where the rearrangement is effected by heating alone, a temperature of about 180° C. is required. On the other hand, irradiation with UV light is effective to promote rearrangement at temperatures as low as about 25° C. The mixture of diacids can be separated (e.g. via the sparingly soluble potassium salt of the E-diacid) but this is generally unnecessary since the Z-fulgide is converted into E-fulgide on heating. Accordingly the mixture can be heated to form the heliochromic compound.

Figure 13:
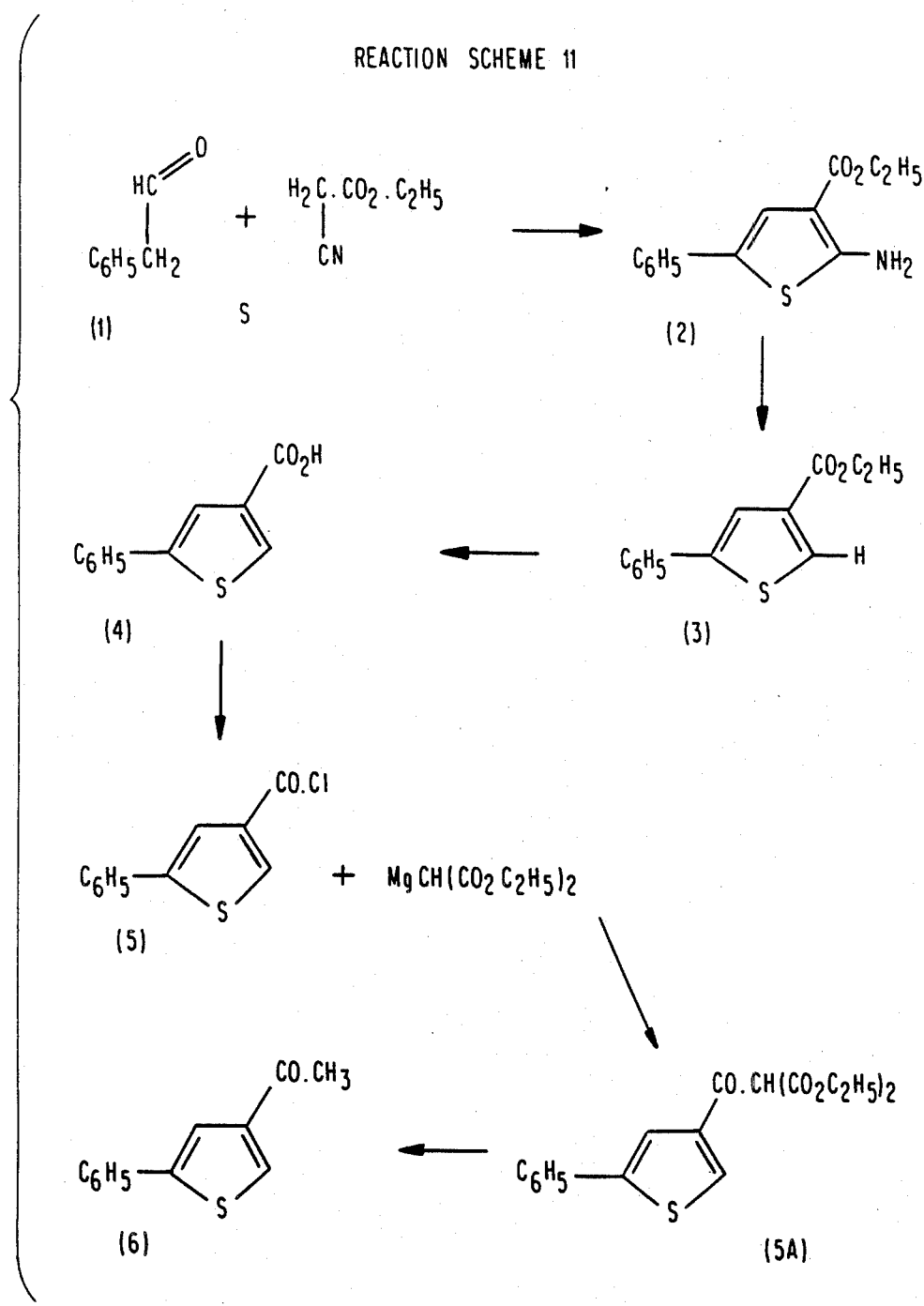

In cases where the thiophen starting materials of general formula (II A) above is not readily obtainable, this may be synthesised by a Gewald type reaction in which an acetaldehyde derivative is condensed with sulphur and ethyl cyanoacetate, preferably in the presence of morpholine and a solvent such as ethanol. The product of this reaction is an amino ester of a thiophen derivative. If the acetaldehyde derivative has an aryl substituent, this will be present as a substituent in the thiophene ring. The thiophene derivative is converted to the corresponding acid chloride by deamination and hydrolysis. The resultant acid chloride is reacted with a salt (e.g. the magnesium salt) of diethyl malonate to yield the corresponding ketone. This process which is a novel procedure is illustrated in Example 18 and FIG. 13 of the formula drawings. Referring to FIG. 13, this illustrates the preparation of 4-acetyl-2-phenylthiophene (6) starting from phenylacetaldehyde (1). Derivatives of compound (6) in which the phenyl group is substituted, e.g. with alkoxy or alkyl, are readily obtained by selection of an appropriate substituted phenyl acetaldehyde starting compound (1) 4 acetyl-2-phenyl-thiophene, and related compounds in which the phenyl group is substituted are novel compounds.

The following Examples are given to illustrate the preparation of heliochromic compounds in accordance with the invention. Reaction schemes showing the formation of the heliochromic compounds from their respective fulgide precursor are given in the accompanying FIGS. 1 to 13, inclusive, identified as reaction schemes 1 to 11. In all cases where it is stated that compounds were irradiated with "white" light, an intense white light source, containing a U.V. component, was used.

EXAMPLE 1

Figure 3:
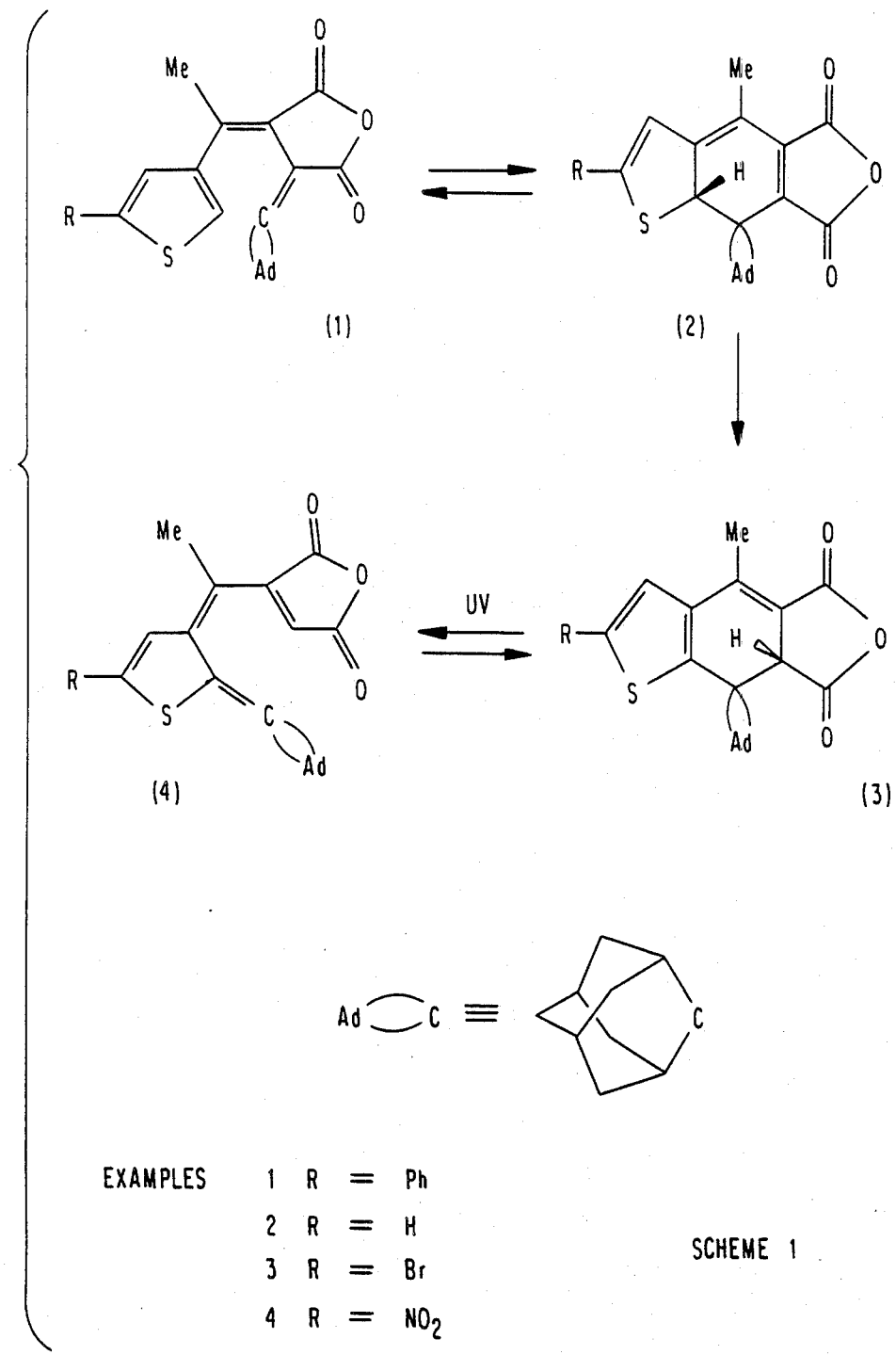

Scheme 1 R=Ph (FIG. 3)

2-Phenyl-4-acetylthiophen (8 g) was condensed with either diethyl or dimethyl adamantylidene succinate (18 g) in toluene (100 cm$^3$), using sodium hydride (6 g) as condensing agent, and gave, after work up and hydrolysis with a slight excess of 10% ethanolic potassium hydroxide solution, the E-diacid as the potassium salt. The diacid, obtained by acidificaion with hydrochloric acid, was cyclised with acetyl chloride (50 cm$^3$) and gave the fulgide of structure (1) as yellow crystals (4.7 g).

On heating the fulgide (1) (4.7 g) at 180° C. in o-dichlorobenzene it cyclised to the coloured 7,7a-dihydrobenzothiophen (7,7a-DHBT) (2) which rearranged to the heliochromic compound (3) (4.4 g) 94% yield, after crystallisation from o-dichlorobenzene. A blue coloured form (4) was obtained by irradiation with white light which reverted rapidly to the colourless form (3) on removal of the white light.

EXAMPLE 2

Scheme 1 R=H (FIG. 3)

3-Acetylthiophen (50 g) was condensed with diethyl adamantylidenesuccinate (142 g) in toluene (400 cm$^3$) using sodium hydride (44 g) as condensing agent and gave, after work up, hydrolysis with 10% ethanolic potassium hydroxide solution and acidification, the E-diacid in 49% yield as well as a mixture of E- and Z-diacids. Cyclisation of the E-diacid with acetic anhydride gave E-fulgide (1) in 75% yield after purification.

On heating the fulgide (1) at 180° C. in o-dichlorobenzene, it rearranged to the heliochromic compound (3), which was isolated in 50–60% yield from unreacted fulgide (1), its Z isomer and thianaphthene (13, Sheet 2) by recrystallisation from o-dichlorobenzene. Heliochromic compound (3) behaved similarly to the compound of Example 1 when irradiated with white light except that the coloured form (4) was purple.

EXAMPLE 3

Scheme 1 R=Br (FIG. 3)

2-Bromo-4-acetylthiophen (15 g) was condensed with diethyl adamantylidenesuccinate (23 g) in toluene (100 cm$^3$) using sodium hydride (6 g) as condensing agent. Work up as described in Example 1, gave the E-fulgide of structure (1), as colourless needles from ethanol (7.5 g).

On irradiation at 366 nm. fulgide (1) in toluene at 110° C. rearranged quantitatively to the heliochromic compound (3), or alternatively, on heating the fulgide (2 g) at 180° C. in o-dichlorobenzene for ½ hour, it rearranged to the heliochromic compound in near quantitative yield. Heliochromic compound (3) reversibly produced a maroon coloured form on irradiation with white light.

EXAMPLE 4

Scheme 1 R=NO$_2$ (FIG. 3)

E-fulgide (1 g), formula (1), R=H, was nitrated with concentrated nitric acid (0.43 g) in acetic anhydride (1.6 g). Work up gave Z-fulgide (0.3 g) and a mixture of E- and Z-fulgides. Irradiation at 366 nm of the Z-fulgide (0.3 g) in toluene at 20° C. caused isomerisation to the E-fulgide (1), (R=NO$_2$) cyclisation to the 7,7a-DHBT (2), (R=NO$_2$) and rearrangement to the heliochromic compound (3), (R=NO$_2$). The coloured form (4) of the heliochromic compound was maroon.

EXAMPLE 5

Figure 4:
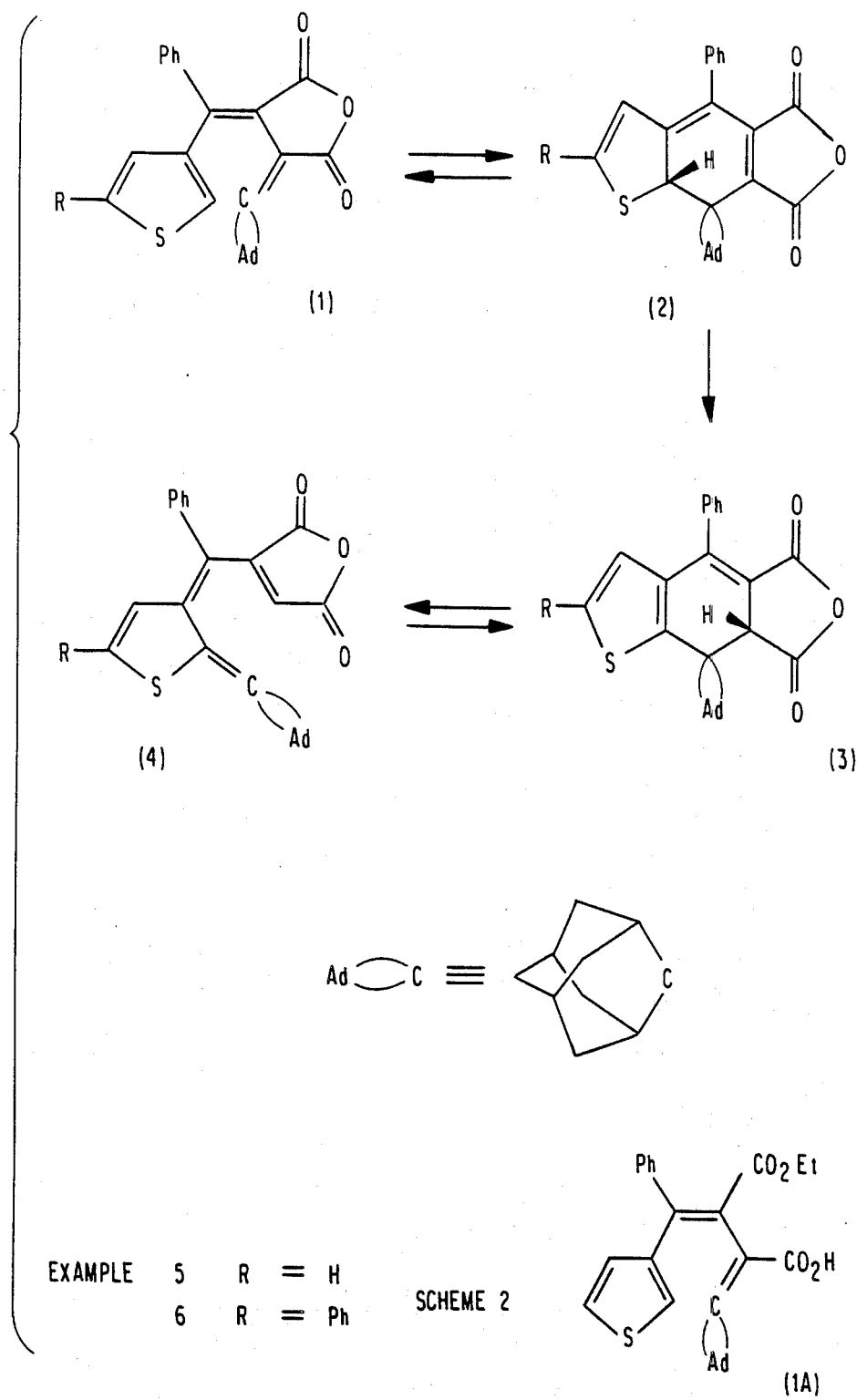

Scheme 2 R=H (FIG. 4)

3-Benzoylthiophen (5 g) was condensed with diethyl adamantylidenesuccinate (8 g) using potassium t-butoxide (3 g) in t-butanol (100 cm$^3$) as condensing agent. The mixture was boiled (1 h), t-butanol was distilled off under reduced pressure and the residue was acidified with hydrochloric acid and extracted with ether. Solvent was removed from the ether extract and the residual half-esters (formula 1A) was hydrolysed with 10% ethanolic potassium hydroxide. The diacids, obtained on acidification, were cyclised with acetic anhydride and gave a mixture of E and Z-fulgides.

The mixed fulgides (10 g) were heated (¾ h) in tetralin (100 cm$^3$) at 208° C. Work up, gave the heliochromic compound (3), (R=H) (7.2 g) after crystallisation from ethanol. Compound (3) had a blue coloured form.

EXAMPLE 6

Scheme 2 R—Ph (FIG. 4)

2-Phenyl-4-benzoylthiophen (13 g) was condensed with dimethyl adamantylidenesuccinate (14 g) in toluene (700 cm$^3$) using sodium hydride (5 g) as condensing agent. A mixture of E and Z fulgides was obtained in the manner described in Example 1.

On heating the mixed fulgides in tetralin, as described in Example 5, the heliochromic compound (3), (R=Ph) was obtained, which had a blue colored form (4).

EXAMPLE 6

Figure 5:
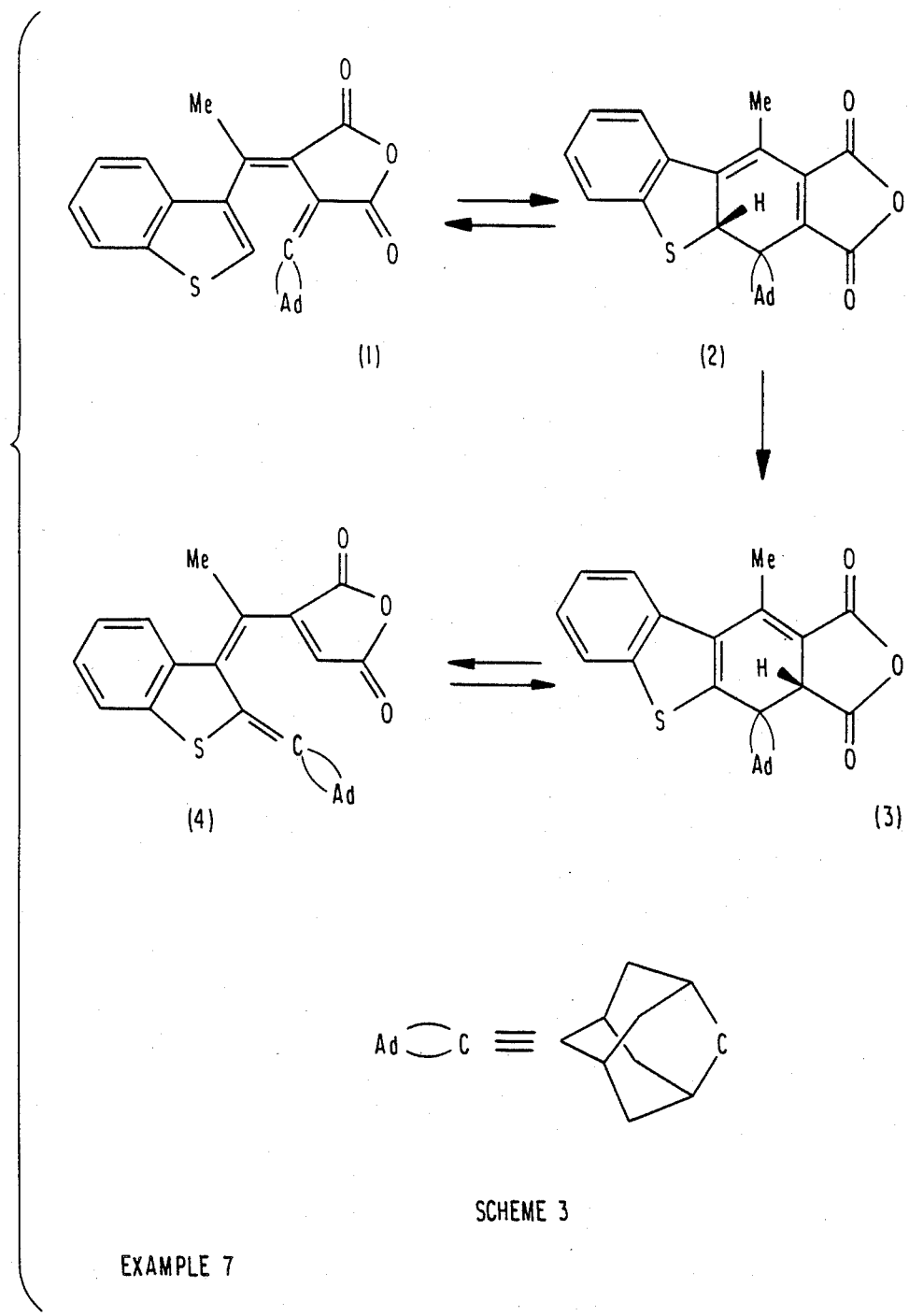
Figure 6:
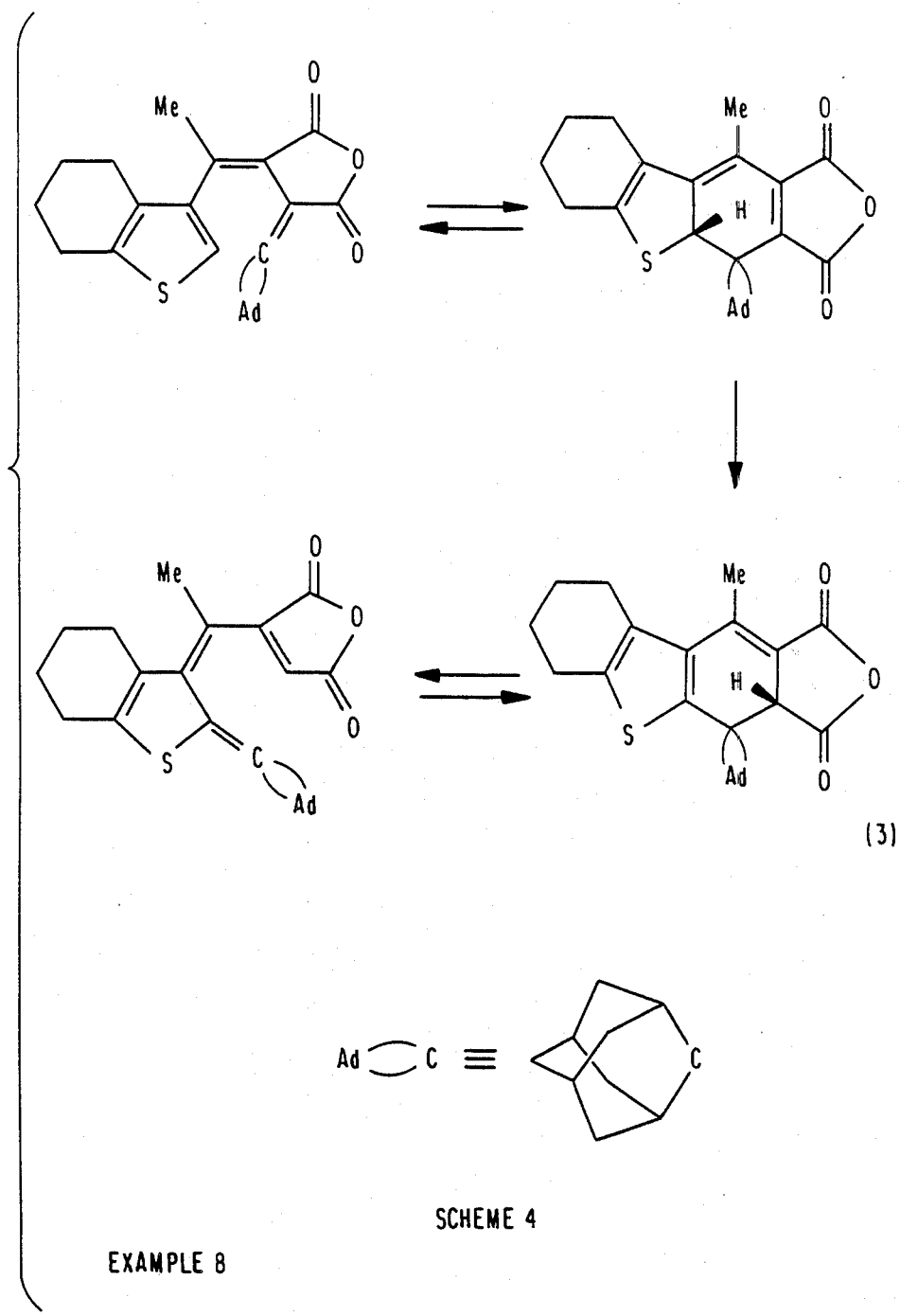

Scheme 3 (FIG. 5)

3-Acetylthianaphthene (18 g) was condensed with diethyl adamantylidenesuccinate (29 g) in toluene (200 cm$^3$) using sodium hydride (11 g) as condensing agent. Work up including hydrolysis, acidification and cyclisation as described in Example 1, gave a mixture of E- and Z-fulgides which could be separated by fractional crystallisation from chloroform and petroleum (bp. 60°–80° C.)

On irradiation, at 366 nm, the E-fulgide (1) in toluene at 20° C., cyclised to form the structure (2) which then rearranged in near quantitative yield to give the heliochromic compound (3), obtained as yellow crystals after crystallisation from chloroform and petroleum (bp. 60°–80° C.). Compound (3) reversibly formed a red compound (4) on irradiation with white light.

EXAMPLE 8

Scheme 4 (Sheet 6)

3-Acetyl-4,5,6,7-tetrahydrothianaphthene (3 g) was condensed with dimethyl adamantylidenesuccinate (6 g) using potassium t-butoxide (3 g) in t-butanol (50 cm$^3$). The mixture was heated (2 h) at 80° C. and worked up as described in Example 5 to give a mixture of E- and Z-fulgides, from which the Z-fulgide was separated by fractional crystallisation from ethanol, pale yellow prisms m.p. 185°–187° C.

On irradiation to 366 nm, Z-fulgide isomerised to the E-fulgide which rearranged to the heliochromic compound (3), as described in Example 7. Compound (3) reversibly coloured blue of irradiation with U.V. light.

EXAMPLE 9

Figure 7:
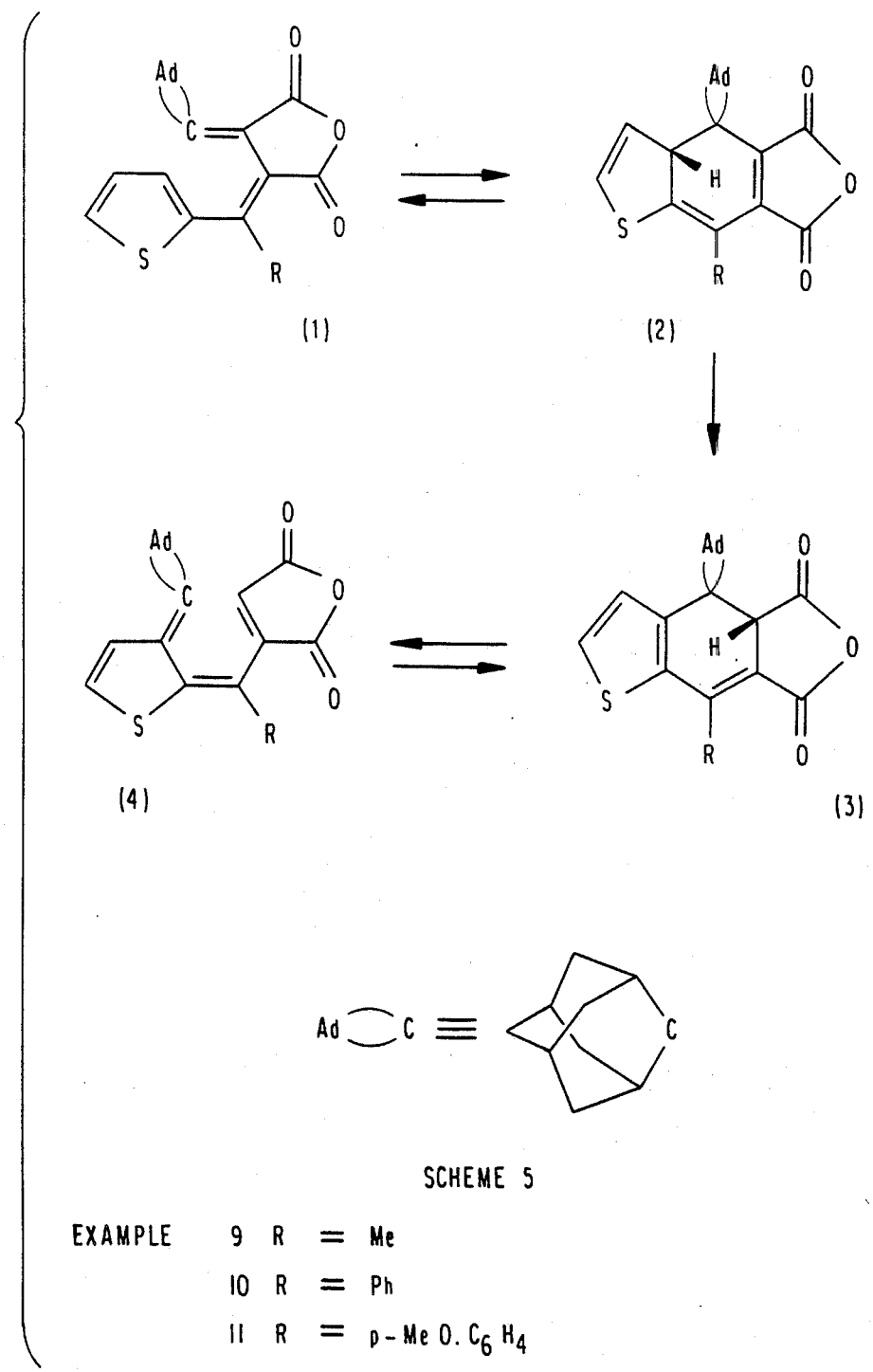

Scheme 5, R=Me (FIG. 7)

2-Acetylthiophen (6 g) was condensed with diethyl adamantylidenesuccinate (16 g) in toluene (60 cm$^3$) in the presence of sodium hydride (5 g). Work up, as described in Example 2, gave E-fulgide (1) in 60% yield after crystallisation from ethanol.

On irradiation at 366 nm, fulgide (1) in toluene rearranged to the heliochromic compound (3) which was purified by chromatography on silica gel using toluene and petrol (1:1) as eluent, and obtained in 70% yield as yellow needles m.p 197°–198° C. from dichloromethane and petrol. On exposure to white light, compound (3) underwent ring opening to form compound (4) which was red. The reverse reaction occurred in the dark.

EXAMPLE 10

Scheme 5 R—Ph (FIG. 7)

2-Benzoylthiophen (10 g) was condensed with diethyl adamantylidenesuccinate (16 g) using potassium t-butoxide (6 g) in t-butanol (80 cm$^3$). Work up, as in Example 5, gave a mixture of pale orange E- and Z-fulgides.

On irradiation at 366 nm, the mixed fulgides in toluene at 55° C. gave the heliochromic compound (3), (R—PH) in 70% yield, which was further purified by chromatography on silica gel using toluene and petrol as eluent, as in Example 9. The coloured form (4) was purple.

EXAMPLE 11

Scheme 5

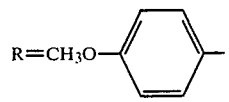

(FIG. 7)

2-p-Methoxybenzoylthiophen (2 g) was condensed with diethyl adamantylidenesuccinate (3 g) using potassium t-butozide (2.5 g) in t-butanol (20 cm$^3$). Work up as in Examples 5 and 10, gave a mixture of bright yellow fulgides in 50% yield.

On irradiation at 366 nm, the mixed fulgides in toluene at 20° C. gave the heliochromic compound (3), as in Example 10, whose coloured form was blue.

EXAMPLE 12

Figure 8:
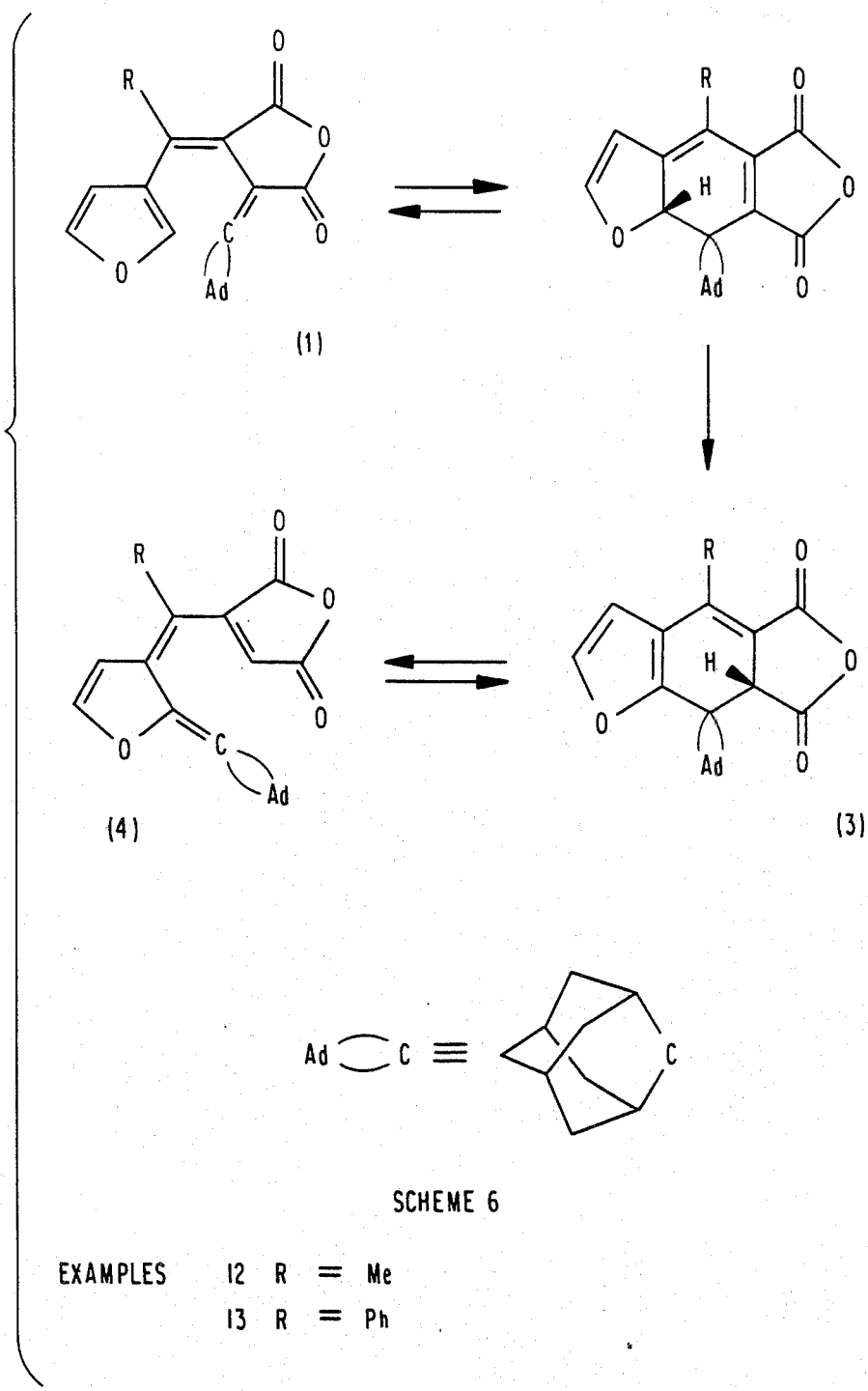

Scheme 6 R=Me (FIG. 8)

3-Acetylfuran (2.5 g) was condensed with diethyl adamantylidenesuccinate (8 g) in toluene (100 cm$^3$) using sodium hydride (2 g) as condensing agent. Work up, gave the E-fulgide (1) (40 mg), as yellow needles, m.p. 160°–161° C. from chloroformand petroleum b.p. 60°–80° C.

On heating (1 h) the E-fulgide at 180° C. in deuterichloroform in a sealed tube, it rearranged to the heliochromic compound (3), obtained as yellow needles, m.p. 210° C. dec., from ether, which reversibly formed a maroon coloured compound (4) on irradiation with white light.

EXAMPLE 13

Scheme 6 R=Ph (FIG. 8)

3-Benzoylfuran (4.5 g) was condensed with diethyl adamantylidenesuccinate (7.3 g) using potassium t-butoxide (8 g) in t-butanol (100 cm$^3$). Work up, as described in Example 5, gave a mixture of E- and Z-fulgides.

The mixed fulgides were converted into the heliochromic compound (3) as described in Example 5, purified by crystallistion from chloroform and petroleum (b.p. 60°–80° C.). The coloured form (4) of the heliochromic compound was blue.

EXAMPLE 14

Figure 9:
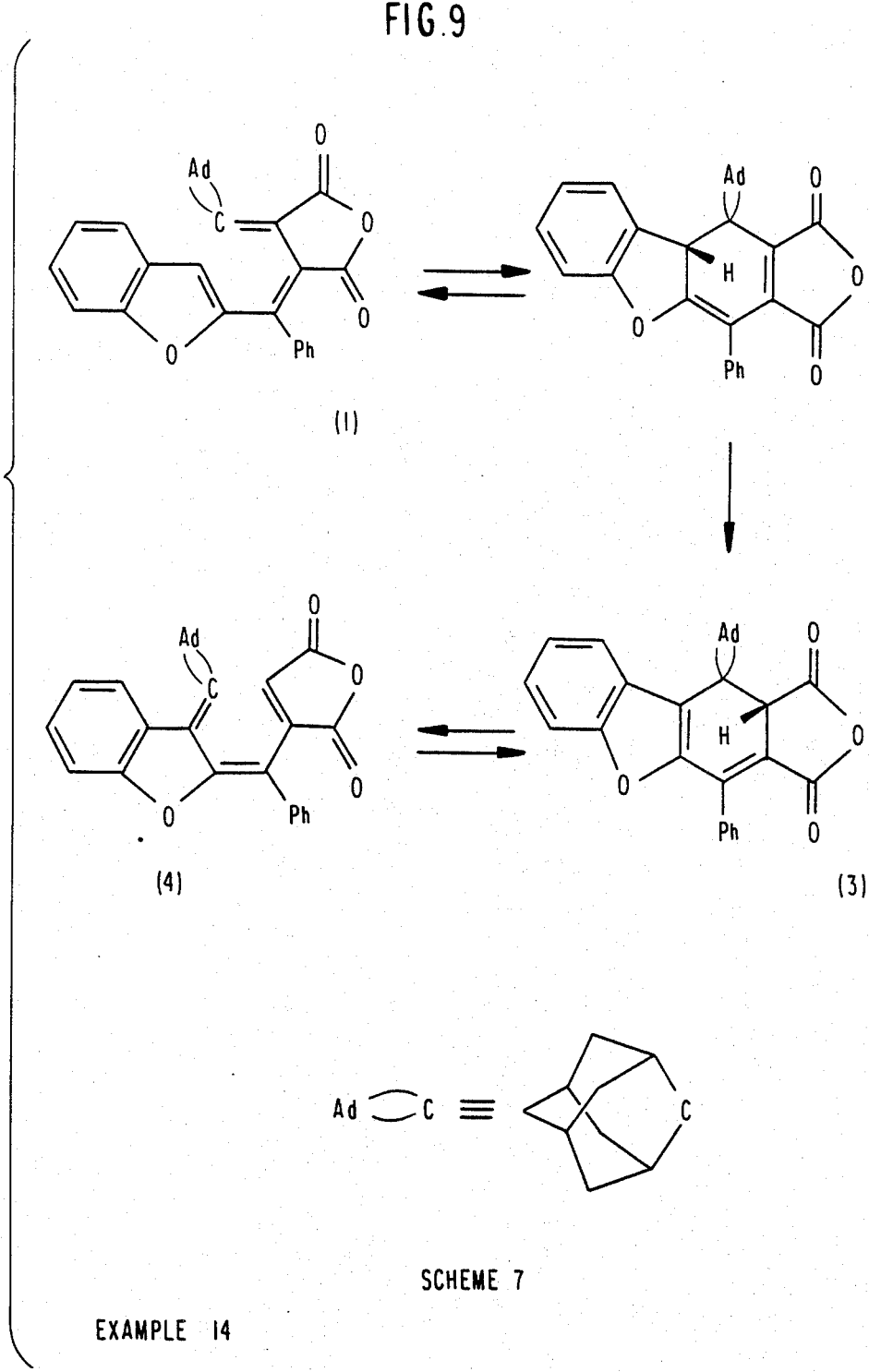

Scheme 7 (FIG. 9)

2-Benzoylbenzofuran (5 g) was condensed with dimethyl adamantylidenesuccinate (8 g) in toluene (100 cm$^3$) using sodium hydride (3 g) as condensing agent. Work up, as in Example 1, but using acetic anhydride (30 cm$^3$) instead of acetyl chloride, with diacid (3 g), gave E-fulgide (1) as yellow crystals from toluene and petroleum (b.p. 60°–80° C.), m.p. 257°–259° C.

On irradiation at 366 nm., fulgide (1) in toluene at 110° C. gave the heliochromic compound (3) which was purified by chromatography on silica gel using toluene and petroleum (1:1 mixture) as eluent. Compound (3) was reversibly converted to a red compound (4) on exposure to white light.

EXAMPLE 15

Figure 10:
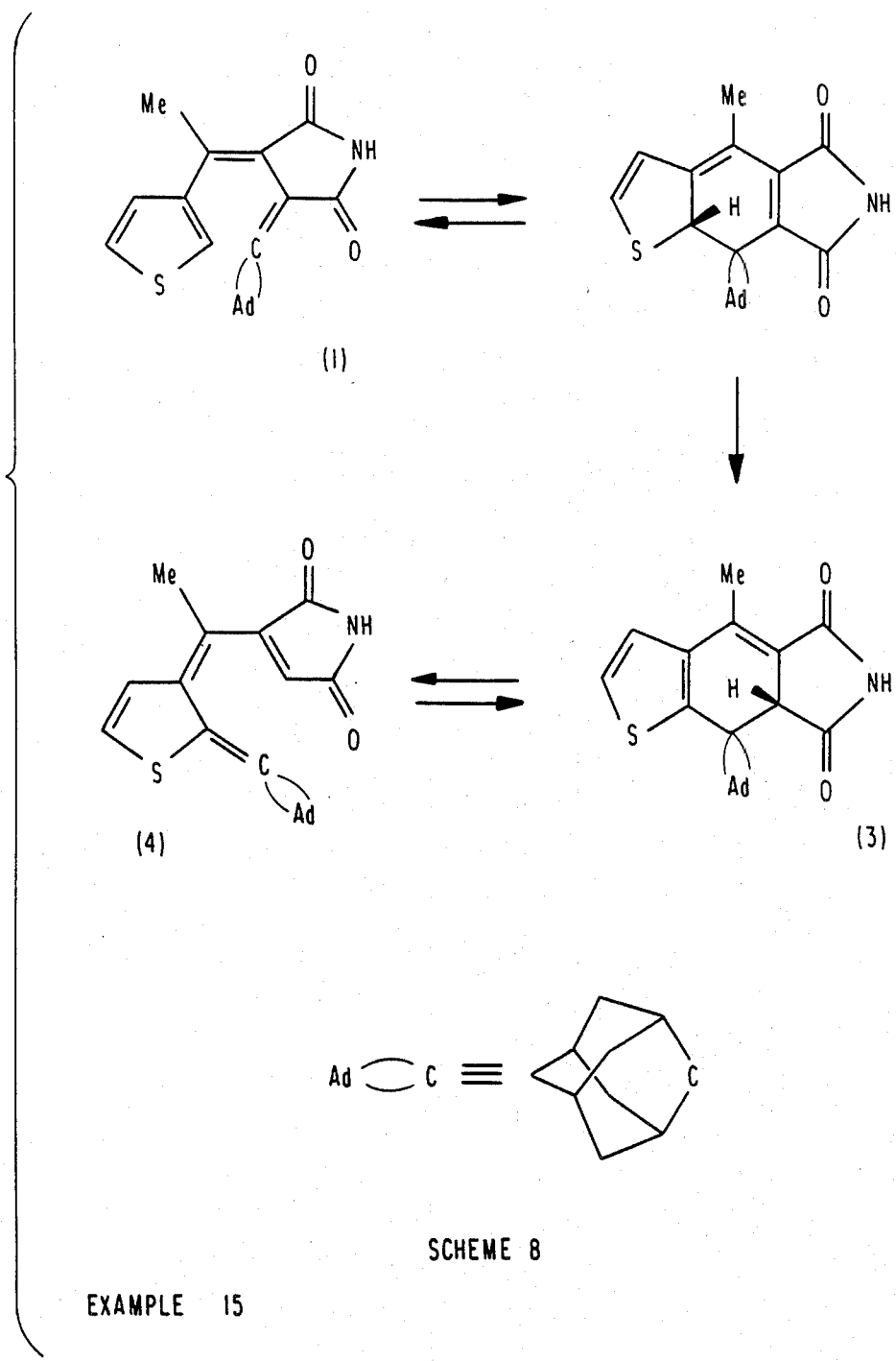

Scheme 8 (FIG. 10)

E-fulgide (1, R=H in Scheme 1) (FIG. 3) (1 g), prepared as in Example 2, in acetone (20 cm$^3$) was treated with 0.880 ammonia (5 cm$^3$). After ½ h, acetone was removed and the residue carefully acidified with 5M hydrochloric acid and extracted with ether. The ethereal extract was dried over anhydrous magnesium sulphate, filtered and ether removed. The resulting acid amide was converted into the methyl ester amide, by reaction with diazomethane in ether and this ester amide was boiled (0.5 h) with methanolic solution of sodium methoxide (freshly prepared by dissolving sodium (0.5 g) in methanol (100 cm$^3$). Work up, gave the E-fulgide (1) (0.65 g), crystals from ethanol.

On irradiation at 366 nm, fulgimide (1) in toluene at 20° C. rearranged to give the heliochromic compound (3). Compound (3) was reversibly convertible to a maroon coloured compound (4) on exposure to white light.

Routes to the correspondng heliochromic imides include rearrangement of the corresponding fulgimides by heating in solvent in an analogous manner to the corresponding fulgides. Alternatively, the heliochromic anhydride could be converted to its corresponding imide by reaction with ammonia or an aliphatic or aromatic amine (see as illustrated in Example 15).

The following Examples also illustrate the preparation of fulgimides and their conversion into heliochromic compounds.

EXAMPLE 16

Figure 11:
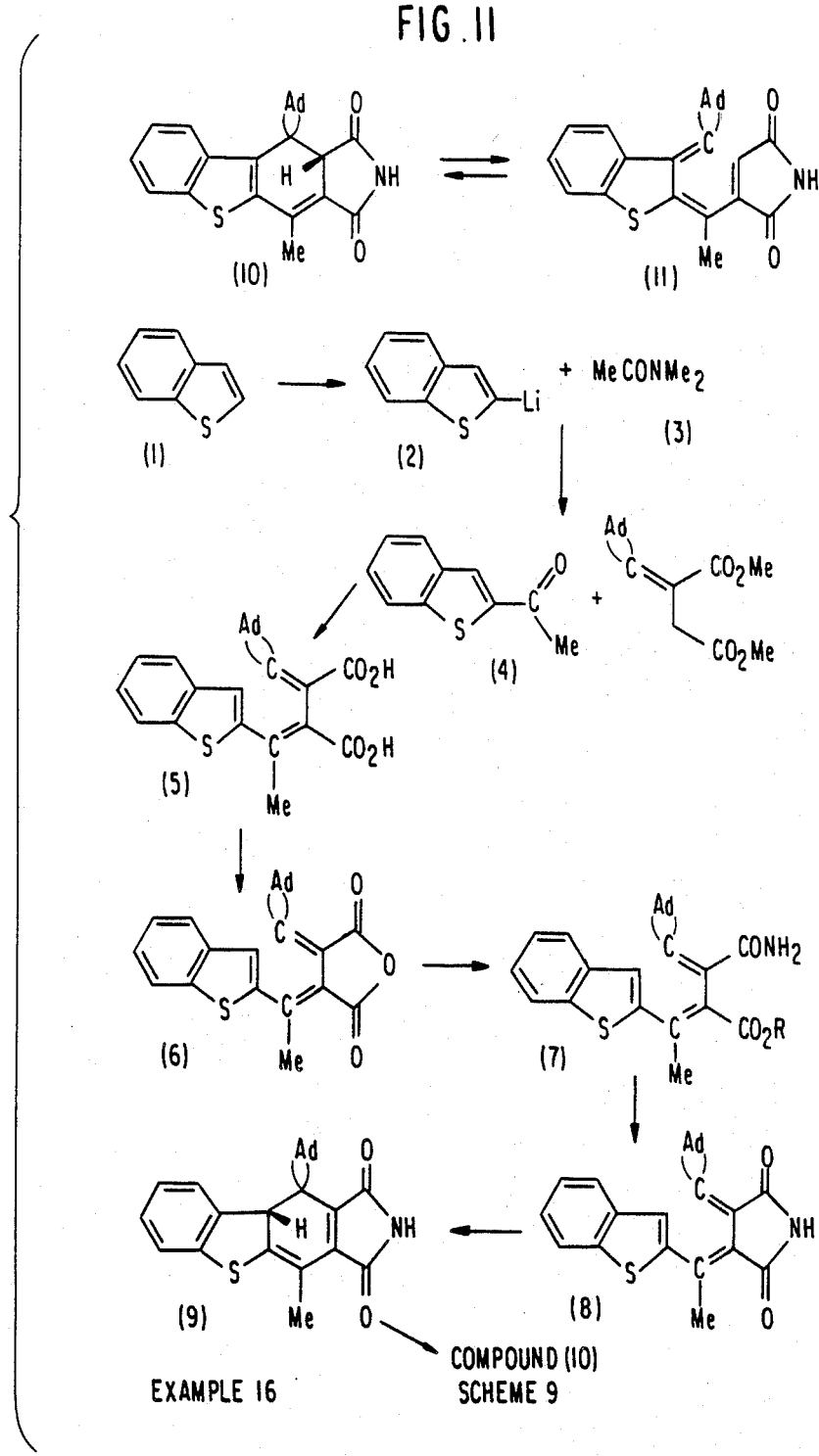

Scheme 9 (FIG. 11)

Benzothiophen (1) in ether was treated with an ethereal solution of butyl lithium and the resulting 2-lithiobenzothiophen (2) was reacted with dimethylacetamide (3). Work up gave 2-acetylbenzothiophen (4), as colourless crystals.

Ketone (4) was condensed with dimethyl adamantylidenesuccinate in the presence of sodium hydride in toluene. The resulting half-ester was hydrolysed with ethanolic potassium hydroxide and acidified with hydrochloric acid to yield diacid (5), which was cyclised to E-fulgide (6), using acetic anhydride.

E-fulgide (6), obtained in bright yellow crystals, was dissolved in acetone and treated with conc.ammonia. The resulting succinamic acid (7, R=H) was converted into the corresponding methyl ester (7, R=Me) using ethereal diazomethane and hence into E-fulgimide (8) by reaction with freshly prepared sodium methoxide in methanol. To monitor the course of reaction by n.m.r. spectroscopy, E-fulgimide (8) was irradiated at 366 nm for 3 days in CDCl$_3$. It photocyclised to photochrome (9) which, in turn, underwent a 1,5-hydrogen shift to yield heliochromic imide (10). Imide (10) can be reversibly converted into an orange-coloured form (11) by U.V. irradiation in toluene. On removal of the U.V. stimulation, the compound (11) reverted to its colourless form (10).

EXAMPLE 17

Figure 12:
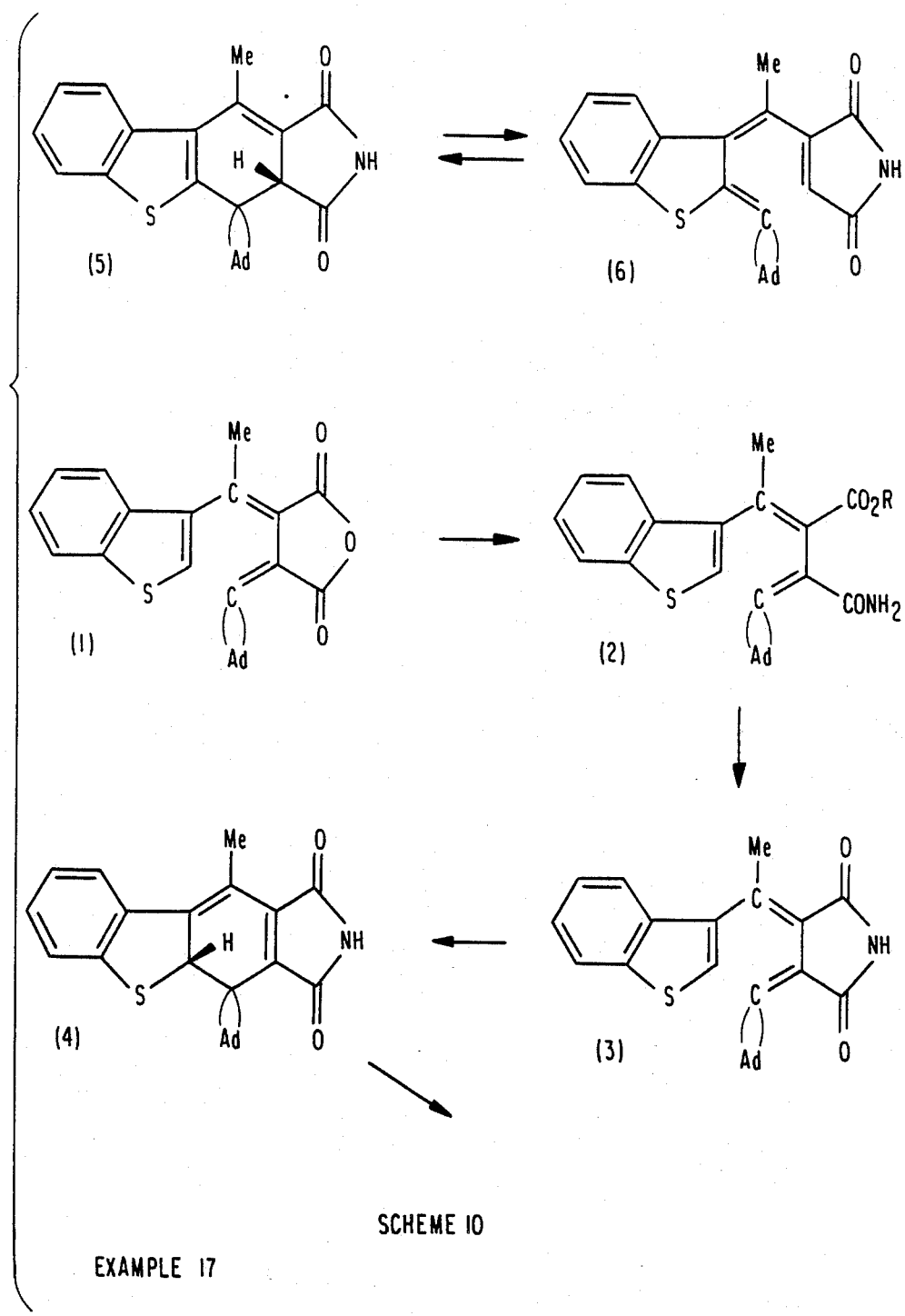

(Scheme 10) (FIG. 12)

Fulgide (1), obtained by the procedure described in Example 8, can be reacted with ammonia in acetone to form the succinamic acid (2)(R=H), followed by treatment with etheral diazomethane to form the corresponding methyl ester. The ester compound (2) (R=Me), can be treated with freshly prepared sodium methoxide in methanol. The resulting fulgimide (3) was photochromic, showing a colourless to red colour change on irradiation at 366 nm, reversed by white light.

On irradiation at 366 nm in CDCl$_3$ for 3 days, fulgimide (3) is converted into heliochromic compound (5) In sunlight, compound (5) undergoes a colourless to orange colour change to compound (6) and thermally fades to the colourless forms.

EXAMPLE 18

1. Preparation of 4-acetyl-2-phenyl thiophene (FIG. 13)

Phenylacetaldehyde (1) (30 g) was reacted with sulphur (6 g) and ethyl cyanoacetate (19 g) in the presence of morpholine (17.5 g) and ethanol (50 ccs) to give the crystalline amino ester (2) (11.6 g).

The amino ester (2) was converted to the diazonium salt and reduced by boiling in ethanol containing finely divided copper to give the pure ester (3). Hydrolysis of the ester with aqueous ethanolic KOH followed by acidification with 5M HCl, gave the acid (4) in approximately 70% yield. The acid was converted to the corresponding acid chloride (5) by reaction with SOCl$_2$.

The acid chloride (5) was reacted with magnesium diethyl malonate to yield the compound (5A) as an intermediate and the ketone (6) as the final product. The resulting ketone can be converted to the corresponding heliochrome as described in Example 1.

EXAMPLE 19

4-acetyl-2-(3'4'-dimethoxyphenyl)thiophene was prepared as described in Example 18 using 3,4-dimethoxyphenyl acetaldehyde as the starting material instead of phenyl acetaldehyde. The resulting methyl ketone (75 g) (compound (6) FIG. 13—phenyl replaced by 3,4-dimethoxy phenyl) was condensed with dimethyl succinate (140 g) in the presence of sodium hydride (100 g) in toluene, followed by hydrolysis to form the diacid. Cyclisation with hot acetic anhydride gave the E-fulgide which was purified by chromatography on silica gel. On irradiation at 366 nm in toluene, the fulgide was converted into the heliochromic compound of formula (3), FIG. 4, R=3,4-dimethoxy phenyl. On exposure to sunlight or to a flash gun the compound turned deep blue.

The heliochromic compounds described herein are solvatochromic i.e. their absorption spectra depends upon the solvent. Thus, in the case of photoreactive lenses, the nature of the colour change can be varied by selecting the plastics material forming the lenses or the coating thereon.

Investigations of the colour fade rate after removal of the U.V. light stimulation, shows that this substantially follows first order kinetics. This is in contrast with the fade rates of known photoreactive lenses based on silver dispersions, whose fade rate decreases rapidly with time so that a very considerable time delay is required before the colour fade is substantially complete.

The heliochromic compounds of this invention can be added to a polymerization mixture from which plastics lenses are intended to be produced. For example, in one test methyl methacrylate (53 cm) containing the heliochrome of formula 9 (FIG. 1) (0.15 g) and benzoyl peroxide (0.15 g) was polymerised by heating at 100° C. for 30 minutes. The resulting polymer was found to be heliochromic, which indicates that the heliochromes are partially resistant to peroxide-induced degradation.

The discovery of photochromic materials which can be used to render plastic lenses photoreactive is a particularly valuable one since, until the present invention, it has not been possible to produce photoreactive plastic lenses which are capable of undergoing more than a small number of colour change cycles. It is possible in principle to incorporate or coat any type of plastics (or glass) lens but generally it is envisaged that the compounds of this invention will be used to render photoreactive the usual types of plastic lenses; these are essentially polycarbonate and alkyl acrylate and methacrylate lenses. Methods of manufacturing plastic lenses are described for example in U.S. Pat. Nos. 3,9344,637, 2,542,386 and 3,404,861, the disclosure of which is incorporated herein by reference.

The most commonly used material for plastic lenses is diethylene glycol bis (allyl carbonate) usually known as CR-39 (CR-39 is a trade mark of P.P.G. Ltd.). The heliochromic compound may be mixed or combined into the CR-39 catalysed liquid monomer, degassed and poured into glass moulds and cured, e.g. as described in U.S. Pat. No. 2,542,286, the disclosure of which is incorporated herein by reference for further details of the procedure for moulding or casting plastic lenses.

A variety of techniques are available for preparing heliochromic plastics articles in accordance with the teaching of this invention. The heliochromic compounds need not be incorporated directly into or coated onto the plastics articles, but can be employed in the form of fulgide or fulgimide precursors and converted in situ, during or after the incorporation or coating step, into the corresponding heliochromic compound, e.g. by heating at U.V. irradiation. Conversion in situ provides an advantageous route to the manufacture of heliochromic plastics articles, such as photoreactive lenses.

It has been found, for example, that an effective amount of precursor is incorporated into a plastics article, such as a lens by contacting in substantially oxygen-free conditions at least one surface of the lens with a melt or solution of the fulgide or fulgimide, which is the precursor of the desired heliochromic compound. Preferably the treatment is effected at elevated temperature, e.g. about 180° C., in order to increase the rate of diffusion of the fulgide or fulgimide into the plastics article. Although at this temperature, the fulgides and fulgimides undergo conversion to the corresponding heliochromic compound, it is believed that the fulgide or fulgimide diffuses preferentially into the plastics article. Possibly this is because the heliochromic compounds tend to have higher melting points than their precursors. In any event, crystals of heliochromic compound are observable in the precursor melts used to treat the preformed plastics articles.

While the precursors may be employed in the form of melts and are generally quite stable in molten condition at a temperature of about 180° C. for a few hours, precursor can also be imbibed into the plastics articles from a solution. Solvents employed should, of course, be inert and are preferably high boiling, e.g. boiling at temperatures above 200° C. so that the imbibation from a solution can be carried out at elevated temperature in order to increase the rate of diffusion.

In the case of solvents, advantage may be taken of a technique employed in disperse dyeing of textiles or fibres where a solvent is selected which possesses a lesser affinity for the solute (in this case the precursor rather than a dyestuff) than does the material to be treated (in this case the plastics article). As a result the precursor is effectively partitioned between solution in the solvent and solid solution in the plastic and thus diffuses into the plastics article. Generally high boiling points solvents such as fluorinated hydrocarbons or silicone oils are suitable from this viewpoint when imbibing the precursor into CR39 plastics articles. Usually a saturated solution of the precursor in the selected solvent is used, which would not normally exceed a concentration of a few percent of the precursor. The following Examples illustrate this aspect of the invention:

EXAMPLE 20

A quantity of the fulgide prepared in Example 2 (FIG. 3, formula (1), R=H) was melted in a concave depression in a hot plate heated to a temperature of 180° C. The surface of a cured CR-39 plastics lens was treated with the molten precursor by laying its convex surface (whose curvature roughly corresponded with the concavity of the depression) in the depression in the hot plate. In this way the surface of the lens was maintained in contact with the molten precursor for 2 hours.

After this treatment the lens was exposed to radiation from an AM 2 lamp at 25° C. and was found to be heliochromic, darkening to 5.5% transmission. On removal of the stimulation from the lamp, the time required to fade to half the initial optical density was 32 seconds. The fatigue life ($T\frac{1}{2}$) was 2000 minutes. $T\frac{1}{2}$ is the time taken for the induced optical density to decay to half its initial value when exposed continuously to Air Mass 2 radiation.

EXAMPLE 21

A saturated solution was prepared of the same fulgide as used in Example 20 in the fluorocarbon solvent sold Minnesota Mining and Manufacturing Company (3M) under the trade name FC 70. This solvent had a boiling point of 217° C. The resulting solution was heated to 180° C. and a 2 mm thick coplanar CR39 lens was immersed in the solution for one hour while maintaining the temperature at 180° C. After removal from the solvent, the lens was found to be heliochromic and darkened to an induced optical density of 0.7 when irradiated with an AM 2 lamp. Thermal reverse was very rapid at ambient temperature when removing the white light irradiation.

Reference is made herein to U.S. patent application Ser. No. 530160 filed Sept. 7, 1983, Baskerville et al which describes preparation of heliochromic plastics articles, such as photoreactive lenses, by incorporating precursors of the heliochromic compounds of this invention into plastic moulding and casting compositions, and forming the heliochromic compound in situ in the plastic article during the moulding or casting step or in an after treatment thereof. The disclosure of the Baskerville application is specifically incorporated herein by reference.

We claim:

1. A compound having the following general formula:

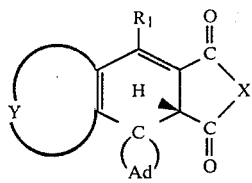
(I)

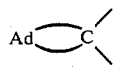

represents an adamantylidene; $R_1$ represents hydrogen, lower alkyl, phenyl or phenyl alkyl;

X represents oxygen or $>NR_2$, in which $R_2$ is hydrogen, lower alkyl, phenyl or phenyl alkyl and

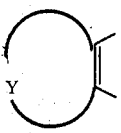

is a 2,5-, 2,4- or 3,5-dimethoxybenzo, a 2- or 3-furano, or a 2- or 3-thiopheno group, which Y groups are unsubstituted or may be substituted by one to four members selected from the group consisting of deuterium, lower alkyl, nitro, halogen, or phenyl.

2. A compound according to claim 1 in which the furano or thiopheno is substituted with one or two members selected from the group consisting of deuterium, lower alkyl, nitro, halogen or phenyl.

3. A compound according to claim 1 in which $R_1$ is a lower alkyl or phenyl group.

4. A compound according to claim 1 in which the ring represented by

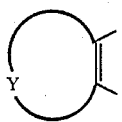

is a thiophenol or furano group.

5. A photoreactive ophthalmic or plano lens having a heliochromic compound coated on a surface thereof or laminated or incorporated in the material of the lens, the heliochromic compound having the property of reversibly forming a coloured structural form on irradiation with U.V. light and returning to a colourless or paler structural form at normal ambient temperature in the absence of U.V. stimulation, the coloured form having the following structure (a)

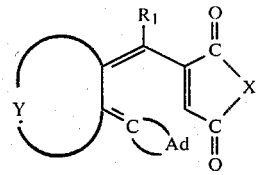
(a)

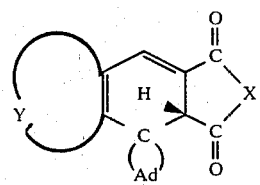
(b)

and being capable of conversion to its colourless or paler form (b) by formation of a central 6-membered ring, wherein

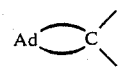

represents an adamentylidene; $R_1$ represents hydrogen, lower alkyl, phenyl, or phenyl alkyl; X represents oxygen or $>NR_2$, in which $R_2$ is hydrogen, lower alkyl, phenyl or phenyl alkyl and

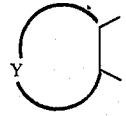

is a 2,5-, 2,4- or 3,5-dimethoxybenzo, a 2- or 3-furano, or a 2- or 3-thiopheno group, which Y groups are unsubstituted or may be substituted by one to four members selected from the group consisting of deuterium, lower alkyl, nitro, halogen, or phenyl.

6. A photoreactive lens according to claim 5 wherein the lens is formed from a polycarbonate or a polyalkyl methacrylate or acrylate.

7. A photoreactive ophthalmic or plano lens which comprises a blend of heliochromic compounds, as claimed in claim 1 or claim 2, coated on a surface thereof or laminated or incorporated in the material of the lens.

* * * * *